United States Patent
Nagy

(10) Patent No.: US 6,984,599 B2
(45) Date of Patent: Jan. 10, 2006

(54) OLEFIN POLYMERIZATION CATALYSTS BASED ON HYDROXYL-DEPLETED CALIXARENE LIGANDS

(75) Inventor: Sandor Nagy, Naperville, IL (US)

(73) Assignee: Equistar Chemicals, LP, Houston, TX (US)

(*) Notice: Subject to any disclaimer, the term of this patent is extended or adjusted under 35 U.S.C. 154(b) by 228 days.

(21) Appl. No.: 10/421,052

(22) Filed: Apr. 23, 2003

(65) Prior Publication Data

US 2004/0214715 A1 Oct. 28, 2004

(51) Int. Cl.
- B01J 31/00 (2006.01)
- B01J 37/00 (2006.01)
- C08F 4/02 (2006.01)
- C08F 4/60 (2006.01)
- C08F 4/06 (2006.01)

(52) U.S. Cl. .............. 502/103; 502/117; 502/171; 502/202; 526/172; 526/134; 526/159

(58) Field of Classification Search ............. 502/102, 502/103, 117, 152, 153, 171, 202, 204, 206, 502/207; 526/172, 134, 159
See application file for complete search history.

(56) References Cited

U.S. PATENT DOCUMENTS

| | | | | |
|---|---|---|---|---|
| 5,153,157 | A | 10/1992 | Hlatky et al. | 502/117 |
| 5,198,401 | A | 3/1993 | Turner et al. | 502/155 |
| 5,241,025 | A | 8/1993 | Hlatky et al. | 526/129 |
| 5,414,180 | A | 5/1995 | Geerts et al. | 585/525 |
| 5,554,775 | A | 9/1996 | Krishnamurti et al. | 556/7 |
| 5,637,660 | A | 6/1997 | Nagy et al. | 526/160 |
| 5,648,440 | A | 7/1997 | Sugano et al. | 526/132 |
| 5,767,034 | A * | 6/1998 | Diaz-Barrios et al. | 502/132 |
| 5,902,866 | A | 5/1999 | Nagy et al. | 526/133 |
| 6,211,311 | B1 | 4/2001 | Wang et al. | 526/131 |
| 6,232,260 | B1 | 5/2001 | Nagy et al. | 502/155 |
| 6,384,229 | B1 | 5/2002 | Hlatky | 548/101 |
| 6,544,918 | B1 | 4/2003 | Nagy et al. | 502/103 |

FOREIGN PATENT DOCUMENTS

EP 0 770 630 5/1997

OTHER PUBLICATIONS

Giannini, et al., *J. Am. Chem. Soc.* 119, (1997) 9198-9210.
Ozerov, et al., *Journal of Organometallic Chemistry* 586, (1999) 223-233.
Kemp, et al., *Journal of Molecular Catalysis A: Chemical* 149, (1999) 125-133.
*Chinese Journal of Chemistry*, 21, (2003) 216-217.
Capacchione, et al., *Inorganic Chemistry Communications* 6, (2003) 339-342.
V. Böhmer, *Angew. Chem. Int. Ed. Engl.* 34, (1995), 713.
Biali et al., *J. Org. Chem.* 56 (1991) 532.
Gutsche et al., *J. Am. Chem. Soc.* 103 (1981) 3782.
Gutsche and Iqbal, *Org. Synth.* 68 (1990) 234-245.
Reinhoudt et al., *J. Chem. Soc., Chem. Commun.* (1990) 1432.

* cited by examiner

Primary Examiner—J. A. Lorengo
Assistant Examiner—J. Pasterczyk
(74) Attorney, Agent, or Firm—Jonathan L. Schuchardt

(57) ABSTRACT

A catalyst system useful for polymerizing olefins is disclosed. The catalyst system includes an organometallic complex that incorporates a Group 3 to 10 transition metal and a hydroxyl-depleted calixarene ligand that is chelated to the metal. Molecular modeling studies reveal that organometallic complexes incorporating such calixarene ligands, when combined with an activator such as MAO, should actively polymerize olefins.

7 Claims, No Drawings

OLEFIN POLYMERIZATION CATALYSTS BASED ON HYDROXYL-DEPLETED CALIXARENE LIGANDS

FIELD OF THE INVENTION

The invention relates to catalysts useful for olefin polymerization. In particular, the invention relates to catalysts based on organometallic complexes that incorporate hydroxyl-depleted calixarene ligands.

BACKGROUND OF THE INVENTION

Ziegler-Natta catalysts are a mainstay for polyolefin manufacture, but single-site (metallocene and non-metallocene) catalysts represent the industry's future. These catalysts are often more reactive than Ziegler-Natta catalysts, and they often produce polymers with improved physical properties.

Single-site catalysts commonly incorporate cyclopentadienyl or "Cp-like" ligands such as indenyl or fluorenyl. A recent trend is to use ligands that can chelate to the transition metal with two or more neutral or anionic electron donors, especially heteroatoms. Examples are bis(allyl) dianions (U.S. Pat. No. 6,544,918), N-oxides (U.S. Pat. No. 6,498,121), neutral multidentate azacyclics (U.S. Pat. No. 6,384,229), or quinolinoxys (U.S. Pat. No. 5,554,775).

"Calixarenes" are a well-known class of cyclic oligomers that are usually made by condensing formaldehyde with p-alkylphenols under alkaline conditions. V. Bohmer summarized the chemistry of calixarenes in an excellent review article (*Angew. Chem., Int. Ed. Engl.* 34 (1995) 713).

Early transition metal complexes in which the four oxygen atoms of calix[4]arenes or O-methylated calix[4]arenes chelate to the metal are now known (see, e.g., *J. Am. Chem. Soc.* 119 (1997) 9198). These complexes have apparently not been used to polymerize olefins.

Because of their unique topology, complexes in which a calixarene ligand coordinates to a transition metal are potentially valuable for olefin polymerization. Too often, olefin polymerization catalysts based on chelating ligands have poor activity. This is consistent with an energetically favorable trans-coordination of the olefin and growing polymer chain in an octahedral or pseudo-octahedral configuration of active sites. Ideally, the growing polymer chain and complexed olefin would be forced into closer proximity. The calixarene framework creates such an opportunity because the aromatic rings prevent trans-coordination. While known oxy-coordinated calixarene complexes (as described in *J. Am. Chem. Soc.* 119 (1997) 9198) have the required topology, electron donation from four oxygens to the metal should preclude significant activity.

Biali et al. (*J. Org. Chem.* 56 (1991) 532 reported a two-step method for making hydroxyl-depleted calix[4] arenes. p-t-Butylcalix[4]-arene is first reacted with diethyl phosphite and triethylamine to give a diphosphate ester. Reductive cleavage of the diester with metallic potassium in liquid ammonia at −78° C., followed by neutralization and chromatographic purification gives a hydroxyl-depleted calixarene (with two hydroxyl groups remaining). Hydroxyl-depleted calixarenes have apparently not been incorporated into transition metal complexes, and they have not been used as components of olefin polymerization catalysts.

The polyolefins industry continues to need new polymerization catalysts. In particular, the industry needs catalysts having activities that rival the activities of single-site catalysts based on cyclopentadienyl, indenyl, and fluorenyl ligands. A valuable catalyst would incorporate ligands that promote a favorable active site configuration in which the complexed olefin and growing polymer chain are forced into close proximity. Ideally, the catalysts could be made economically using well-established synthetic routes.

SUMMARY OF THE INVENTION

The invention is a catalyst system useful for polymerizing olefins. The catalyst system comprises an activator and an organometallic complex. The complex incorporates a Group 3–10 transition metal and a hydroxyl-depleted calixarene ligand that is chelated to the metal. Molecular modeling studies reveal that organometallic complexes incorporating the calixarene ligands, when combined with an activator such as MAO, should actively polymerize olefins.

DETAILED DESCRIPTION OF THE INVENTION

Catalyst systems of the invention include an organometallic complex and an activator. The complex contains a Group 3–10 transition metal. "Transition metal" as used herein includes, in addition to the main transition group elements, elements of the lanthanide and actinide series. More preferred complexes include a Group 4 transition metal.

The organometallic complex includes a hydroxyl-depleted calixarene ligand that is chelated to the metal. As noted earlier, calixarenes are a well-known class of cyclic oligomers that are most conveniently prepared by condensing phenols and formaldehyde. The reaction conditions are conveniently adjusted to provide calixarenes having four, six, or eight phenolic units that are joined by methylene bridges in the cyclic structure. For details about how to synthesize calix[4]arenes, calix[6]arenes, and calix[8]arenes, see Gutsche et al., *J. Am. Chem. Soc.* 103 (1981) 3782 and *Org. Synth.* 68 (1990) 234–245. Preferred calixarenes derive from p-alkylphenols such as p-t-butylphenol.

The procedures referenced above give calixarenes having a full complement of phenolic hydroxyl groups. "Hydroxyl-depleted" calixarenes are most conveniently generated by converting one or more of the —OH groups of a calixarene to —H groups. Preferably, at least about half of the hydroxyl groups in the calixarene are removed. In one suitable approach, developed by Biali et al. (*J. Org. Chem.* 56 (1991) 532), the calixarene reacts with enough phosphorylating agent to covert a portion of the hydroxyl groups to phosphate esters. The esters are cleaved with metallic alkali metal (potassium or sodium) in liquid ammonia at low temperature. After quenching the reaction mixture, the desired partially hydroxyl-depleted calixarene is isolated and purified. A similar approach was reported by Reinhoudt et al. (*J. Chem. Soc., Chem. Commun.* (1990) 1432).

The hydroxyl-depleted calixarene "chelates" to the transition metal, i.e., it bonds to the metal using two oxygens—preferably two alkoxy groups—from the calixarene. Consequently, this face of the complex is no longer available for coordination by either a growing polymer chain or the olefin to be polymerized. The tighter space available for the active site should make the complexes polymerize olefins more efficiently.

The framework of the calixarene ligand can be substituted with other atoms that do not interfere with the ability of the ligand to form complexes with transition metals. For example, the framework of the calixarene ligand can be substituted with alkyl, aryl, halide, alkoxy, thioether, alkylsilyl, or other groups.

Preferably, the calixarene has four, six, or eight phenolic moieties; thus preferred calixarenes are calix[4]arenes, calix[6]arenes, and calix[8]arenes. Calix[4]arenes are more preferred. In preferred catalyst systems, the calixarene ligand is a p-alkylcalixarene, more preferably a p-t-butylcalixarene. The synthetic procedures for making these materials have been finely honed and optimized, and the starting materials, e.g., p-t-butylphenol, are readily available.

The procedures for incorporating the hydroxyl-depleted calixarenes into transition metal complexes are straightforward. Usually, two hydroxyl groups of the calixarene are deprotonated using any suitable base, and the resulting bis(alkoxide) is reacted with a transition metal source to give the complex. Deprotonation methods are well known. Suitable bases include, for example, alkyllithium compounds (e.g., methyllithium or n-butyllithium), alkali metals (e.g., sodium metal), alkali metal hydrides (e.g., potassium hydride), and Grignard reagents (e.g., methyl magnesium chloride or phenyl magnesium bromide). Usually, about two equivalents of the deprotonating agent and about one equivalent of the calixarene precursor are used to produce the ligand. Deprotonation can be performed at any suitable temperature, preferably at or below room temperature. While the deprotonation reaction can be performed at temperatures as low as −78° C. or below, it is preferred to perform this step at room temperature. In another approach, the hydroxyl-depleted calixarene and transition metal source are combined in the presence of a base such as sodium hydroxide or potassium carbonate and warmed if needed to complete the reaction.

The organometallic complexes can be conveniently prepared according to methods that are well known in the art. In general, the complexes are made by combining the deprotonated ligand with a transition metal source. Any convenient source of transition metal can be used. For example, the complexes can be made from transition metal halides, alkyls, alkoxides, acetates, amides, or the like. A particularly convenient source of the transition metal is the transition metal halide. For example, one can use titanium tetrachloride, zirconium tetrachloride, cyclopentadienylzirconium trichloride, vanadium(III) chloride-tetrahydrofuran complex (VCl$_3$(THF)$_3$), titanium (III) chloride-THF complex, chromium(III) chloride-THF complex, cobalt(II) chloride, nickel(II) bromide, platinum(II) chloride, allylnickel (II) chloride dimer, palladium(II) chloride, lanthanum(III) chloride, titanium(III) acetate, or the like. Complexes can also be prepared from salts with labile groups, such as tetrakis(acetonitrile)palladium(II) bis(tetrafluoroborate).

The transition metal complexes are easy to make. Usually, the transition metal source (halide, e.g.) is dissolved or suspended in an organic solvent and the deprotonated ligand is carefully added at any desired temperature, preferably from about −78° C. to about room temperature. Refluxing is used if needed to complete the reaction. Insoluble by-products, if any, can be removed by filtration, solvents are evaporated, and the transition metal complex is isolated, washed, and dried. The resulting complex can generally be used without further purification. Example 1 below illustrates a typical method for making the organometallic complex.

In addition to the hydroxyl-depleted calixarene ligand, the organometallic complex may include additional labile anionic ligands such as halides, alkyls, alkaryls, aryls, dialkylaminos, or the like. Particularly preferred are halides, alkyls, and alkaryls (e.g., chloride, methyl, benzyl). Polymerization-stable ligands, such as cyclopentadienyl, indenyl, fluorenyl, boraaryl, indolyl, indenoindolyl, quinolinoxy, pyridinoxy, or the like, can also be present. For examples of the heteroaryl ligands, see U.S. Pat. Nos. 5,554,775, 5,902,866, 5,637,660, and 6,232,260, the teachings of which are incorporated herein by reference.

In sum, a variety of organometallic complexes incorporating hydroxyl-depleted calixarene ligands are readily accessible for use in catalyst systems of the invention. The complexes and methods discussed herein for making them are merely illustrative, and those skilled in the art will readily recognize or devise many alternative synthetic methodologies.

The catalyst systems include an activator. Suitable activators help to ionize the organometallic complex and activate the catalyst. Suitable activators are well known in the art. Examples include alumoxanes (methyl alumoxane (MAO), PMAO, ethyl alumoxane, diisobutyl alumoxane), alkylaluminum compounds (triethylaluminum, diethyl aluminum chloride, trimethylaluminum, triisobutylaluminum), and the like. Suitable activators include acid salts that contain non-nucleophilic anions. These compounds generally consist of bulky ligands attached to boron or aluminum. Examples include lithium tetrakis(pentafluorophenyl)borate, lithium tetrakis(pentafluorophenyl)aluminate, anilinium tetrakis(penta-fluorophenyl)borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl) borane, riphenylborane, tri-n-octylborane, and the like. These and other suitable boron-containing activators are described in U.S. Pat. Nos. 5,153,157, 5,198,401, and 5,241,025, the teachings of which are incorporated herein by reference. Suitable activators also include aluminoboronates—reaction products of alkyl aluminum compounds and organoboronic acids—as described in U.S. Pat. Nos. 5,414,180 and 5,648,440, the teachings of which are incorporated herein by reference.

The optimum amount of activator needed relative to the amount of organometallic complex depends on many factors, including the nature of the complex and activator, whether a supported catalyst is used, the desired reaction rate, the kind of polyolefin product, the reaction conditions, and other factors. Generally, however, when the activator is an alumoxane or an alkyl aluminum compound, the amount used will be within the range of about 0.01 to about 5000 moles, preferably from about 10 to about 500 moles, of aluminum per mole of transition metal, M. When the activator is an organoborane or an ionic borate or aluminate, the amount used will be within the range of about 0.01 to about 5000 moles, preferably from about 0.1 to about 500 moles, of activator per mole of M.

The activator is normally added to the reaction mixture at the start of the polymerization. However, when a supported catalyst system is used, the activator can be deposited onto the support along with the organometallic complex.

The catalyst systems are optionally used with an inorganic solid or organic polymer support. Suitable supports include silica, alumina, silica-aluminas, magnesia, titania, clays, zeolites, or the like. The support is preferably treated thermally, chemically, or both prior to use to reduce the concentration of surface hydroxyl groups. Thermal treatment consists of heating (or "calcining") the support in a dry atmosphere at elevated temperature, preferably greater than about 100° C., and more preferably from about 150 to about 600° C., prior to use. A variety of different chemical treatments can be used, including reaction with organo-aluminum, -magnesium, -silicon, or -boron compounds. See, for example, the techniques described in U.S. Pat. No. 6,211,311, the teachings of which are incorporated herein by reference.

The complex and activator can be deposited on the support in any desired manner. For instance, the components can be dissolved in a solvent, combined with a support, and stripped. Alternatively, an incipient-wetness technique can be used. Moreover, the support can simply be introduced into the reactor separately from the complex and activator.

The loading of complex on the support varies depending upon a number of factors, including the identities of the complex and the support, the type of olefin polymerization process used, the reaction conditions, and other concerns. Usually, the amount of complex used is within the range of about 0.01 to about 10 wt.% of transition metal based on the amount of supported catalyst. A more preferred range is from about 0.1 to about 4 wt. %.

Catalyst systems of the invention are useful for polymerizing olefins. Preferred olefins are ethylene and $C_3$–$C_{20}$ α-olefins such as propylene, 1-butene, 1-hexene, 1-octene, and the like. Mixtures of olefins can be used. Ethylene and mixtures of ethylene with $C_3$–$C_{10}$ α-olefins are especially preferred.

Many types of olefin polymerization processes can be used. Preferably, the process is practiced in the liquid phase, which can include slurry, solution, suspension, or bulk processes, or a combination of these. High-pressure fluid phase or gas phase techniques can also be used. The process of the invention is particularly valuable for solution and slurry processes.

The olefin polymerizations can be performed over a wide temperature range, such as about –30° C. to about 280° C. A more preferred range is from about 30° C. to about 180° C.; most preferred is the range from about 60° C. to about 100° C. Olefin partial pressures normally range from about 15 psig to about 50,000 psig. More preferred is the range from about 15 psig to about 1000 psig.

The following examples merely illustrate the invention. Those skilled in the art will recognize many variations that are within the spirit of the invention and scope of the claims.

EXAMPLE 1

Preparation of Organometallic Complex 3 p-t-Butylcalix[4]arene (1) is prepared by the method of Gutsche and Iqbal (*Org. Synth.* 68 (1990) 238) by reacting p-t-butylphenol with formalin in the presence of sodium hydroxide. A hydroxyl-depleted calixarene (2) is then produced using the two-step method of Biali et al. (*J. Org. Chem.* 56 (1991) 532). Thus, 1 is phosphorylated using $HPO(OEt)_2$ and triethylamine in carbon tetrachloride at 0° C. The product, which has two phosphate groups, is then reacted with metallic potassium in liquid ammonia at –78° C. to effect reductive cleavage and a net "dehydroxylation" to give hydroxyl-depleted calix[4]arene 2.

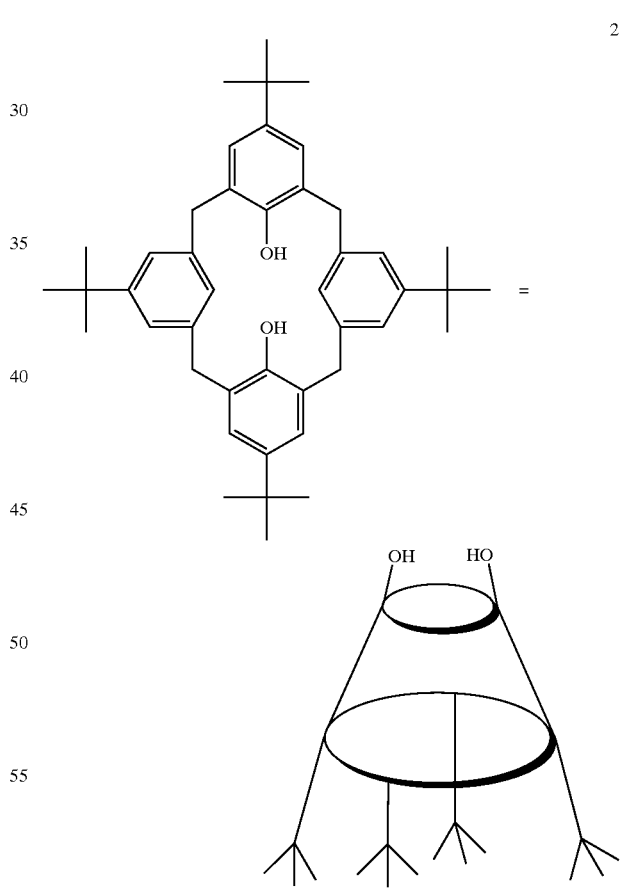

A sample of calix[4]arene 2 (616 mg, 1.0 mmol) is dissolved in dry tetrahydrofuran (20 mL). n-Butyllithium (1.30 mL of 1.6 M solution in hexane; 2.1 mmol, 2.1 eq.) is added at 0° C. with vigorous stirring. The resulting dilithium salt is combined with a mixture of zirconium tetrachloride bis(tetrahydrofuran) complex (377 mg, 1.0 mmol) in dry tetrahydrofuran (10 mL), and the mixture is stirred overnight at room temperature. Volatiles are removed in vacuo. The residue is dissolved in toluene, filtered, and concentrated to give the zirconium complex, which should have structure 3:

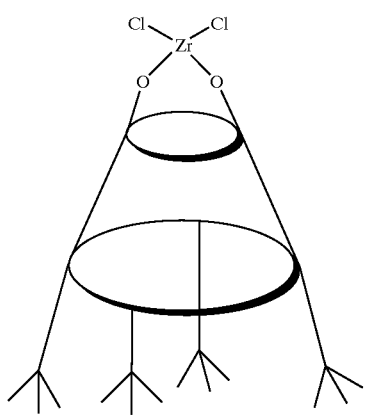

EXAMPLE A

Polyethylene Preparation

Methyl alumoxane (5 mL of 10 wt. % MAO in toluene) is added to a 100-mg sample of the organometallic complex prepared in Example 1. The mixture is injected into a 1.7-L stainless-steel autoclave containing dry, deoxygenated isobutane (850 mL) and triisobutylaluminum (0.2 mmol). The autoclave is heated to 80° C. and is pressurized with ethylene (150 psi). After 1 h, the autoclave is cooled, isobutane is flashed off. The resulting product should be polyethylene.

Molecular Modeling Study

Additional evidence for the suitability of hydroxyl-depleted calixarene ligands for olefin polymerization catalysts comes from molecular modeling studies. All calculations have been performed with complete geometry optimization using the DFT model B3LYP with the LACVP** pseudopotential basis set as incorporated into the TITAN™ software package.

To estimate the effect of hydroxyl-depleted calixarene ligands (L) on the relative stability of the zirconocenium active sites, we use the relative enthalpy ($\Delta\Delta H_f$) of the reaction:

LZrMeEt------->LZrEt$^+$+Me$^-$ compared with the enthalpy of a standard process in which the zirconium is bonded to two cyclopentadienyl ligands:

Cp$_2$ZrMeEt------->Cp$_2$ZrEt$^+$+Me$^-$

According to these estimates (Table 1), hydroxyl-depleted calix[4]arene ligand 5 should stabilize an electrophilic active site as effectively as bis(cyclopentadienyl), and somewhat less effectively compared with indenyl(Cp), fluorenyl(Cp), or bis(fluorenyl).

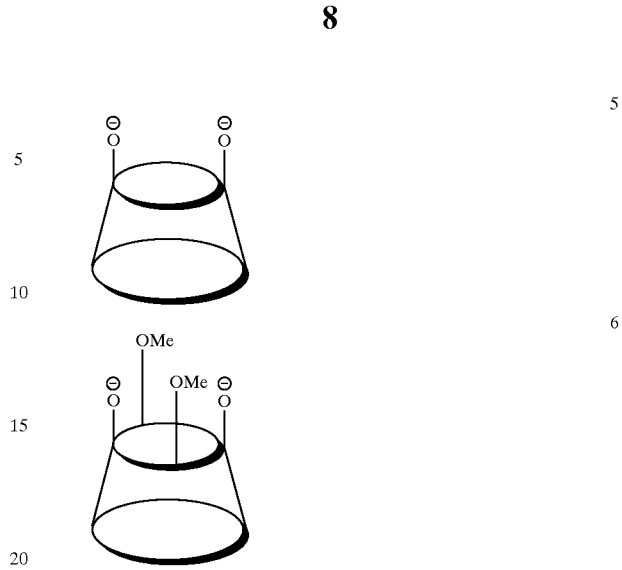

TABLE 1

| Complex | $\Delta\Delta H_f$, kcal/mole |
|---|---|
| Cp$_2$ZrMeEt | 0 |
| (Ind)(Cp)ZrMeEt | −5.0 |
| (Flu)(Cp)ZrMeEt | −8.0 |
| Flu$_2$ZrMeEt | −14 |
| (5)ZrMeEt | 0 |
| (6)ZrMeEt | −34 |

With an active site that is about as stable as bis(cyclopentadienyl) zirconocenes, complexes from hydroxyl-depleted calixarenes such as 5 should permit a high concentration of active sites in the polymerization process. In contrast, calixarenes that are not hydroxyl-depleted, such as O-methylated ligand 6, should over-stabilize the active site (−34 kcal/mol relative to bis(cyclopentadienyl)); consequently, these catalysts should have low activities.

The calculations indicate a minor penalty (4.6 kcal/mol) relative to bis(cyclopentadienyl) in the reactivity of the complex from hydroxyl-depleted calixarene 5 toward ethylene, as characterized by the calculated heat of interaction upon pi-complexation (Table 2). The active site from the complex that incorporates 5 has a higher estimated energy of pi-complexation compared with the baseline complexes, but the energy input needed is only slightly greater (4.6 versus 4.3 kcal/mol) than that required for the bis(fluorenyl) complex. In contrast, the O-methylated calixarene 6 has a much higher energy barrier (15.3 kcal/mol) to pi-complexation, which can be attributed at least in part to greater steric crowding at the active site.

TABLE 2

| Active site | Relative heat of interaction of active site with ethylene, kcal/mol |
|---|---|
| Cp$_2$ZrEt+ | 0 |
| (Ind)(Cp)ZrEt+ | 1.9 |
| (Flu)(Cp)ZrEt+ | 1.9 |
| Flu$_2$ZrEt+ | 4.3 |
| (5)ZrEt+ | 4.6 |
| (6)ZrEt+ | 15.3 |

What is claimed is:

1. A catalyst system which comprises an activator and a complex, wherein the complex comprises a Group 4 transition metal and a hydroxyl-depleted calixarene ligand that is chelated to the metal.

2. The catalyst system of claim 1 wherein the activator is selected from the group consisting of alkyl alumoxanes, alkylaluminum compounds, aluminoboronates, organoboranes, ionic borates, and ionic aluminates.

3. A process which comprises polymerizing one or more olefins in the presence of a catalyst system of claim 1.

4. The catalyst system of claim 1 wherein the hydroxyl-depleted calixarene ligand is a p-alkylcalixarene.

5. The catalyst system of claim 1 wherein the hydroxyl-depleted calixarene ligand is selected from the group consisting of calix[4]arenes, calix[6]arenes, and calix[8]arenes.

6. The catalyst system of claim 1 wherein the hydroxyl-depleted calixarene ligand has the structure:

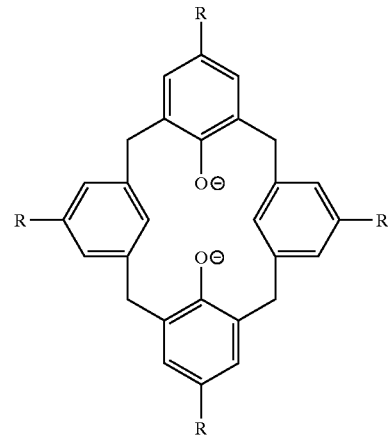

wherein each R is independently hydrogen or a $C_1$–$C_{10}$ alkyl or $C_6$–$C_{10}$ aryl group.

7. The catalyst system of claim 6 wherein each R is tert-butyl.

* * * * *